(12) United States Patent
Durga et al.

(10) Patent No.: US 6,290,933 B1
(45) Date of Patent: Sep. 18, 2001

(54) HIGH CLEANING DENTIFRICE

(75) Inventors: Gary A. Durga, Edison; Michael Prencipe, Princeton Junction; Peter J. Priolo, Highland Park; Peter Ren, Martinsville, all of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/567,402

(22) Filed: May 9, 2000

(51) Int. Cl.[7] .................. A61K 7/16; B24C 1/00; C09G 1/00
(52) U.S. Cl. .............. 424/49; 51/308; 423/335; 423/339
(58) Field of Search .............. 424/49–58; 423/335, 423/339; 51/308

(56) References Cited

U.S. PATENT DOCUMENTS

| | | | |
|---|---|---|---|
| 4,153,680 * | 5/1979 | Seybert | 424/49 |
| 4,312,845 * | 1/1982 | Wason | 423/339 |
| 5,589,160 * | 12/1996 | Rice | 424/49 |
| 5,603,920 * | 2/1997 | Rice | 424/49 |
| 5,651,958 * | 7/1997 | Rice | 424/49 |
| 5,658,553 * | 8/1997 | Rice | 424/49 |
| 5,676,932 * | 10/1997 | Wason et al. | 424/49 |
| 5,716,601 * | 2/1998 | Rice | 424/52 |
| 5,869,028 * | 2/1999 | McGill et al. | 424/49 |
| 5,891,421 * | 4/1999 | McGill et al. | 424/49 |
| 5,932,191 * | 8/1999 | Chevallier et al. | 424/52 |
| 5,939,051 * | 8/1999 | Santalucia et al. | 424/49 |

* cited by examiner

*Primary Examiner*—Shep K. Rose
(74) *Attorney, Agent, or Firm*—Paul Shapiro

(57) ABSTRACT

A high cleaning low abrasion dentifrice containing a silica hydrogel having a mean particle size from about 5 to about 11 microns; an Einlehner hardness of from 1 to about 20; an oil absorption of about 40 to less about 100 cc/g, a BET surface area from 100 to 700 m2/g of silica, the particles having a morphology characterized by glass conchoidal fracture surfaces whereby, the dentifrice composition has a RDA of 110 to 200 and a PCR from about 150 to about 300.

9 Claims, 1 Drawing Sheet

HIGH CLEANING DENTIFRICE

FIELD OF THE INVENTION

This invention relates to dentifrice compositions containing a silica abrasive, which provides improved oral cleaning and a safe level of abrasivity.

BACKGROUND OF THE INVENTION

Synthetically produced silicas play an important role as an ingredient in many of today's toothpaste formulations. Such silicas are relatively safe, nontoxic, ingredients which are compatible with other toothpaste ingredients, including glycerin, sorbitol (or xylitol), thickening agents, detergents, coloring and fragrance materials and optionally fluoride and other actives, whereby the silica acts as an abrasive to clean teeth, remove plaque and food debris.

As an abrasive, silicas debride and physically scrub the external surface of the teeth. This scrubbing action removes the organic film (i.e. the pellicle), formed of salivary proteins which covers the teeth and which is known to become stained and discolored by foods, such as coffee, tea and berries, as well as, by tobacco smoke, cationic antibacterials, and chromogenic bacteria. Such physical removal of the stained pellicle is a simple and effective means of removing the undesirable surface staining and discoloration which occurs daily. Further, such physical removal of the pellicle also removes plaque bacteria on the pellicle surface.

Synthetic silicas include both silica gels and precipitated silicas which are prepared by the neutralization of aqueous silicate solutions with a strong mineral acid. In the preparation of silica gel, a silica hydrogel is formed which is then typically washed to low salt content. The washed hydrogel may be milled to the desired size, or otherwise dried, ultimately to the point where its structure no longer changes as a result of shrinkage. When preparing such synthetic silicas, the objective is to obtain abrasives which provide maximal cleaning (i.e. removal of stained pellicle) with minimal damage to the tooth enamel and other oral tissue. Dental researchers are continually concerned with identifying synthetic silicas meeting these objectives.

U.S. Pat. No. 4,153,680 and GB Patent Application 2,038,303A both disclose the general use of silica hydrogels or hydrated silica gels as dentifrice polishing agents. U.S. Pat. No. 4,632,826 discloses the use of hydrated silica gels in combination with a weakly calcined alumina polish, to form a combination abrasive system. U.S. Pat. Nos. 4,943,429, 5,176,899 and 5,270,033 provide lists of alternative polishing agents, such lists including hydrated silica gels.

U.S. Pat. No. 5,939,051 discloses dentifrice compositions prepared with silica gels having low abrasion and high cleaning products. However, the silica gels have a low particle size distribution of from 2 to 4 microns in order to achieve the low abrasive properties. Manufacturing such small particle size silica gel is energy intensive and relatively costly.

U.S. Pat. Nos. 5,658,553 and 5,651,958 disclose dentifrice compositions containing a combination of precipitated silica and silica gels having high cleaning and low abrasion as indicated by their low radioactive dentin abrasion (RDA) values. Due to the low abrasive nature of the silicas described in U.S. Pat. Nos. 5,651,958 and 5,658,553 the composition inherently has limited cleaning ability.

RDA value is a dental art recognized method of determining the abrasiveness of dentifrice formulations and is determined according to the method recommended by the American Dental Association as set forth by Hefferren, Journal of Dental Research, Volume 55, Issue 4, July–August 1976, pp. 563–573, and described in the Wason U.S. Pat. Nos. 4,340,583, 4,420,312 and 4,421,527.

In spite of the extensive prior art relating to silica hydrogels and other abrasive compounds used to prepare dentifrice compositions for oral cleaning, there is still a need for additional compositions providing improved pellicle cleaning, improved removal of plaque and food debris, all with minimal abrasion of the tooth enamel and other oral tissue.

It is known in the dental art that increasing the RDA value of a dentifrice composition above 110 does not result in a corresponding increase in the cleaning performance of the dentifrice, as measured by Pellicle Cleaning Ratio (PCR), an in vitro method used to measure the efficacy of removing tea and coffee tooth stains relative to a standard. The PCR values referred to herein are obtained by a modification of the method described in "In Vitro Removal of Stain with Dentifrice", G. K. Stookey, et al J. Dental Research, 61, 123–9, 1982. The modification of the PCR method used herein is described in U.S. Pat. No. 5,658,553 and 5,651,958. In this modification, a clear pellicle material is applied to a bovine tooth first, which is then stained with a combination of the pellicle material and tea, coffee and $FeCl_3$ whereas in the original method described by Stookey et al, both pellicle and stain are applied simultaneously.

It has now surprisingly been found that by the practice of the present invention the PCR value of a dentifrice composition can be made significantly higher than those reported in the prior art. In fact, PCR values from 150 to 300 can be achieved at RDA values from 110 to 200 when using the silica hydrogel abrasive of the present invention it being noted that RDA values of 110 to RDA of 250 (maximum allowable) are well within the acceptable abrasivity standards set by the US Federal Drug Administration as well as the American Dental Association, pursuant to the Federal Register (Anticaries Over-The-Counter Drug Products), vol. 45, No. 62, 1980, and vol. 60, No. 194, 1995.

SUMMARY OF THE INVENTION

In accordance with the present invention there is provided a dentifrice composition having superior cleaning functionality, which dentifrice composition, comprises:

(a) an orally acceptable dentifrice vehicle containing from about 5 to about 30% by weight silica hydrogel particles, the particles containing about 10 to about 35% by weight water having:
  (i) a mean particle size from about 5 to about 12 microns;
  (ii) an Einlehner hardness of from 1 to about 20;
  (iii) an oil absorption value of from about 40 to less than 100 cc/100 g;
  (iv) a BET surface area from 100 to 700 $m^2/g$ of silica, the morphology of the particles being characterized by glass conchoidal fracture surfaces, whereby the dentifrice composition has an RDA of from 110 to 200, and a PCR of from about 150 to about 300.

Mean particle size is measured using a Malvern Particle Size Analyzer, Model Mastersizer S, Malvern Instruments, Inc., Southborough, Mass. 01772 wherein a helium-neon gas laser beam is projected through a transparent cell which contains the silica hydrogel particles suspended in an aqueous solution. Light rays which strike the particles are scattered through angles which are inversely proportional to the particle size. The photodetector array measures the quantity of light at several predetermined angles. Electrical signals proportional to the measured light flux values are then processed by a microcomputer system, against a scatter pattern predicted from theoretical particles as defined by the refractive indices of the sample and aqueous dispersant to determine the particle size distribution of the silica hydrogel.

Einlehner hardness value is obtained using Einlehner At-1000 Abrader to measure the softness of the silica hydrogel in the following manner: A Fourdrinier brass wire screen is weighed and exposed to the action of a 10% aqueous silica hydrogel suspension for a given number of revolutions. The hardness value is expressed as milligrams weight lost of the Fourdrinier wire screen per 100,000 revolutions.

BET surface area is determined by a BET nitrogen adsorption method described in Brunauer et al., J. Am. Chem. Soc., 60, 309 (1938). The BET measurement is preformed using an Accelerated Surface Area and Porosimetry Analyzer (ASAP 2400), by Micromeritics Instrument Corporation, Norcross, Georgia 30093. The sample is outgassed under vacuum at 350° C. for a minimum of 2 hours before measurement.

Oil absorption values are measured using the ASTM rub-out method D281. All measurement levels are by weight of the total composition, unless otherwise indicated, such as the case of PCR and RDA values, which are unitless. Additionally, all measurements are made at 25° C., unless otherwise specified.

DETAILED DESCRIPTION OF THE INVENTION

Silica Hydrogel

The silica hydrogel of the present invention is comprised of colloidal particles of silica having an average particle size ranging from about 3 microns to about 12 microns, and more preferably between about 5 to about 10 microns and a pH range from 4 to 10 preferably 6 to 9 when measured as a 5% by weight slurry.

The silica hydrogel used to prepare the dentifrice compositions of the present invention are differentiated by means of their oil absorption values, having oil absorption values of less than 100 cc/100 g, and preferably in the range of from 45 cc/100 g silica to less than 70 cc/100 g silica.

Figure 1:
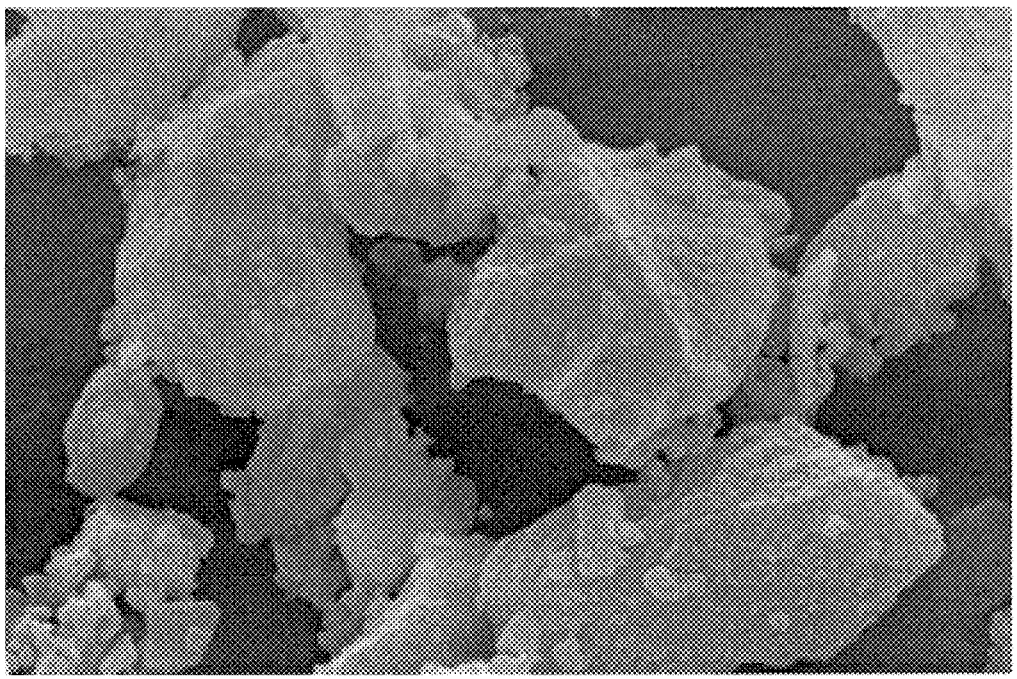
FIG. 1 is a scanning electronphotomicrograph, (SEM) 10,000×magnification, of silica particles of 7–10 microns mean particle size (Sylodent XWA 650) of the present invention having glass conchoidal fracture surfaces.

The silica hydrogel used in the present composition can be further differentiated by the morphology or shape of its particles which are characterized by glass conchoidal fracture surfaces as shown in FIG. 1 of the drawings.

Preparation of the silica hydrogels of the present invention is known in the art, for example, in U.S. Pat. No. 4,153,680 and U.K. Patent Application GB 2,038,303A, the hydrous silica gels being the result of the reaction of an alkali silicate solution with an $SiO_2$ concentration of about 6 to 20 percent by weight in the presence of a mineral acid, such as sulfuric acid, hydrochloric acid, nitric acid, or phosphoric acid. Sodium or potassium silicate may be used as the alkali silicate, with sodium silicate being preferred. The acid is added to the alkali silicate solution until a pH of less than 10 to 11 is reached. The resulting product is a solid silica which includes the water within its pores. After the silica hydrogel is formed it is washed, until a purity level of about 98% $SiO_2$ is obtained (the remaining impurity being sulfate salts). The resulting silica hydrogel is milled to the desired 3 to 10 microns in diameter particle size and dried to a water content of from 10 to 35% by weight, preferably about 20 to 30% by weight, to yield the desired silica hydrogel.

A silica hydrogels useful in the practice of the present invention is marketed under the trade designation Sylodent XWA by Davison Chemical Division of W.R. Grace & Co., Baltimore, Md. 21203. Sylodent 650 XWA a silica hydrogel shown in FIG. 1 is composed of particles of colloidal silica having a water content of 29% by weight averaging from about 7 to about 10 microns in diameter, having an Einlehner hardness of 2, a BET surface area of 390 $m^2$/g of silica, an oil absorption of less than 70 $cm^3$/100 g of silica.

The RDA of the silica hydrogel abrasive dentifrice of the present invention is from 110 to 200, preferably from about 120 to about 170.

The PCR of the silica hydrogel compositions of the present invention, a measurement of the cleaning characteristics of dentifrices, generally ranges from about 150 to 300 and is preferably greater than about 160.

The silica hydrogel abrasive can be used as the sole abrasive in preparing the dentifrice composition of the present invention or in combination with other known dentifrice abrasives or polishing agents. Commercially available abrasives may be used in combination with the silica hydrogel and include precipitated silicas having a mean particle size of up to about 20 microns, such as Zeodent 115, marketed by J.M. Huber Chemicals Division, Havre de Grace, Maryland 21078, or Sylodent 783 also marketed by Davison Chemical Division of W.R. Grace & Co. Other useful dentifrice abrasives include sodium metaphosphate, potassium metaphosphate, tricalcium phosphate, dihydrated dicalcium phosphate, aluminum silicate, calcined alumina, bentonite or other siliceous materials, or combinations thereof.

The total quantity of abrasive present in the dentifrice compositions of the present invention is at a level of from about 5% to about 40% by weight, preferably from about 5% to about 30% by weight when the dentifrice composition is a toothpaste. Higher levels, as high as 95%, may be used if the dentifrice composition is a toothpowder.

Dentifrice Vehicle

The orally-acceptable dentifrice vehicle used to prepare the dentifrice composition comprises a water-phase, containing a humectant therein. The humectant is preferably glycerin, sorbitol, xylitol, and/or propylene glycol of molecular weight in the range of 200–1,000; but, other humectants and mixtures thereof may also be employed. The humectant concentration typically totals about 5 to about 70% by weight of the oral composition.

Reference hereto to sorbitol refers to the material typically commercially available as a 70% aqueous solution. Water is present typically in amount of at least about 10% by weight, and generally about 25 to 70% by weight of the oral composition. Water employed in the preparation of commercially suitable toothpastes should preferably be deionized and free of organic impurities. These amounts of water include the free water which is added plus that which is introduced with other materials such as with sorbitol.

The dentifrice compositions of the present invention can contain a variety of optional dentifrice ingredients. As described below, such optional ingredients can include, but are not limited to, thickening agents, surfactants, a source of fluoride ions, a synthetic anionic polycarboxylate, a flavoring agent, additional antiplaque agents, and coloring agents.

Thickening Agents

Thickeners used in the compositions of the present invention include natural and synthetic gums and colloids, examples of which include carrageenan (rish moss), xanthan gum and sodium carboxymethyl cellulose, starch, polyvinylpyrrolidone, hydroxyethylpropyl cellulose, hydroxybutyl methyl cellulose, hydroxypropylmethyl cellulose, and hydroxyethyl cellulose. Inorganic thickeners include amorphous silica compounds which function as thickening agents and include colloidal silicas compounds available under trademarks such as Cab-o-sil fumed silica manufactured by Cabot Corporation and distributed by Lenape Chemical, Bound Brook, N.J; Zeodent 165 from J.M. Huber Chemicals Division, Havre de Grace, Md. 21078; and Sylox 15, also known as Sylodent 15, available from Davison Chemical Division of W.R. Grace Corporation, Baltimore, Md. 21203. The thickening agent is present in the dentifrice composition in amounts of about 0.1 to about 10% by weight, preferably about 0.5 to about 4% by weight.

Surfactants

Surfactants are used in the compositions of the present invention to achieve increased prophylactic action and render the dentifrice compositions more cosmetically acceptable. The surfactant is preferably a detersive material which imparts to the composition detersive and foaming properties. Suitable examples of surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, sodium lauryl sulfoacetate, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine. The surfactant is typically present in the dentifrice compositions of the present invention in an amount of about 0.3 to about 5% by weight, preferably about 0.5 to about 2% by weight.

Fluoride and Other Active Agents

The dentifrice composition of the present invention may also contain a source of fluoride ions or fluorine-providing component, as anticaries agent in amount sufficient to supply about 25 ppm to 5,000 ppm of fluoride ions and include inorganic fluoride salts, such as soluble alkali metal salts, for example, sodium fluoride, potassium fluoride, sodium fluorosilicate, ammonium fluorosilicate, sodium monofluorophosphate, as well as tin fluorides, such as stannous fluoride and stannous chloride. Sodium fluoride is preferred.

In addition to fluoride compounds, there may also be included antitartar agents such as pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$ long chain polyphosphates such as sodium hexametaphosphate and cyclic phosphates such as sodium trimetaphosphate. These antitartar agents are included in the dentifrice composition at a concentration of about 1 to about 5% by weight.

Another active agent useful in dentifrice compositions of the present invention are antibacterial agents, which can be from 0.2 to 1.0% by weight of the dentifrice composition. Such useful antibacterial agents include non-cationic antibacterial agents which are based on phenolic or bisphenolic compounds, such as halogenated diphenyl ethers such as triclosan (2,4,4'-trichloro-2'-hydroxydiphenyl ether).

Anionic Polycarboxylate

Synthetic anionic polycarboxylates may also be used in the dentifrice compositions of the present invention as an efficacy enhancing agent for any antibacterial, antitartar or other active agent within the dentifrice composition. Such anionic polycarboxylates are generally employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methylvinyletherlmaleic anhydride having a molecular weight (M.W.) of about 30,000 to about 1,800,000 most preferably about 30,000 to about 700,000. Examples of these copolymers are available from GAF Corporation under the tradename Gantrez, e.g. AN 139 (M.W. 500,000), AN 119 (M.W. 250,000); S-97 Pharmaceutical Grade (M.W. 700,000), AN 169 (M.W. 1,200,000–1,800,000), and AN 179 (M.W. above 1,800,000); wherein the preferred copolymer is S-97 Pharmaceutical Grade (M.W. 700,000).

When present, the anionic polycarboxylates is employed in amounts effective to achieve the desired enhancement of the efficacy of any antibacterial, antitartar or other active agent within the dentifrice composition. Generally, the anionic polycarboxylates is present within the dentifrice composition from about 0.05% to about 4% by weight, preferably from about 0.5% to about 2.5% by weight.

FLAVOR

The dentifrice composition of the present invention may also contain a flavoring agent. Flavoring agents which are used in the practice of the present invention include essential oils as well as various flavoring aldehydes, esters, alcohols, and similar materials. Examples of the essential oils include oils of spearmint, peppermint, wintergreen, sassafras, clove, sage, eucalyptus, majoram, cinnamon, lemon, lime, grapefruit, and orange. Also useful are such chemicals as menthol, carvone, and anethole. Of these, the most commonly employed are the oils of peppermint and spearmint.

The flavoring agent is incorporated in the dentifrice composition at a concentration of about 0.1 to about 5% by weight and preferably about 0.5 to about 1.5% by weight.

Other Ingredients

Various other materials may be incorporated in the dentifrice compositions of this invention, including desensitizers, such as potassium nitrate; whitening agents, such as hydrogen peroxide, calcium peroxide and urea peroxide; preservatives; silicones; and chlorophyll compounds. These additives, when present, are incorporated in the dentifrice composition in amounts which do not substantially adversely affect the properties and characteristics desired.

Preparation Of The Dentifrice

The preparation of dentifrices is well known in the art, such as described in U.S. Pat. Nos. 3,996,863, 3,980,767, 4,328,205 and 4,358,437, which are incorporated herein by reference. More specifically, to prepare a dentifrice of the present invention, generally the humectants e.g. glycerin, sorbitol, propylene glycol, and polyethylene glycol; are dispersed in the water in a conventional mixer under agitation. Into the dispersion are added the organic thickeners, such as carboxymethyl cellulose (CMC), carrageenan, or xanthan gum; any anionic polycarboxylate; any salts, such as sodium fluoride anticaries agents; and any sweeteners; the resultant mixture is agitated until a homogeneous gel phase is formed. Into the gel phase are added a pigment such as $TiO_2$, and any acid or base required to adjust the pH. These ingredients are mixed until a homogenous phase is obtained. The mixture is then transferred to a high speed/vacuum mixer, wherein, the inorganic thickener, such as Zeodent 165; and surfactant ingredients are added to the mixture. The silica hydrogel of the present invention is added at this point, along with other abrasives to be used in the composition. Any water insoluble antibacterial agent, such as triclosan, is solubilized in the flavor oils to be included in the dentifrice and the solution is added along with the surfactants to the mixture, which is then mixed at high speed for from 5 to 30 minutes, under vacuum of from about 20 to 50 mm of Hg, preferably about 30 mm Hg. The resultant product is in each case a homogeneous, semi-solid, extrudable paste or gel product.

The following example further describes and demonstrates preferred embodiments within the scope of the present invention. The example is given solely for illustration, and are not to be construed as limitation of this invention as many variations thereof are possible without departing from its spirit and scope.

EXAMPLE

A silica dentifrice composition of the present invention, designated "Composition 1" was prepared with a 20% by weight total abrasive content as listed in Table I below consisting of a combination of a the silica hydrogel Sylodent XWA 650 having the morphology shown in FIG. 1.

Figure 2:
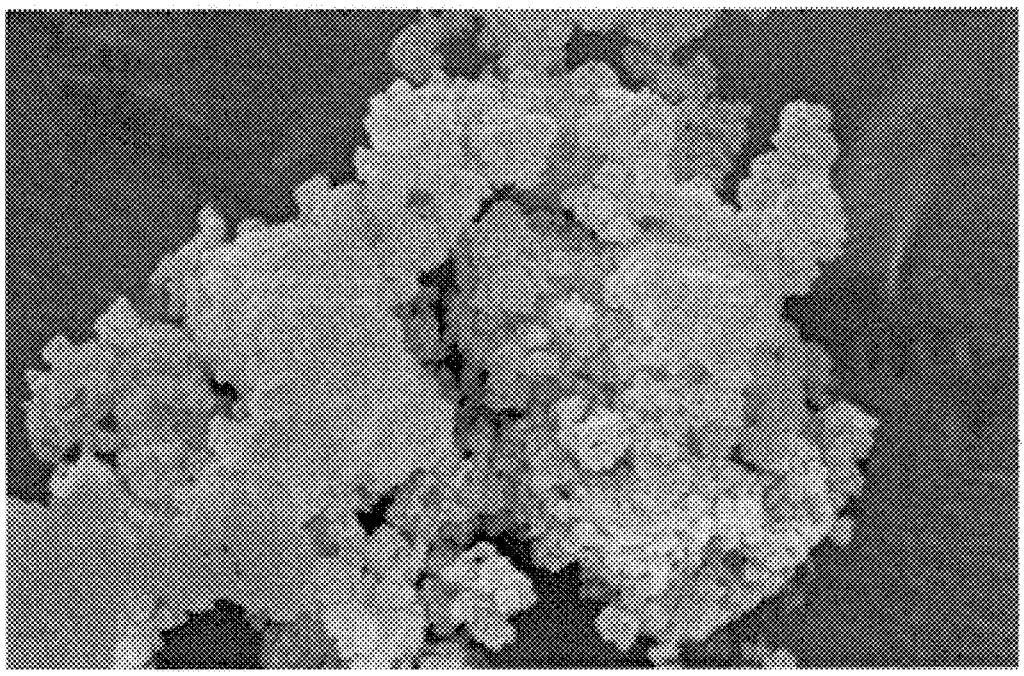
FIG. 2 is a SEM (10,000×magnification) of a precipitated silica abrasive (Zeodent 115) having a structure consisting of a copressed agglomeration of spherical shapes surrounded by a loose fitting agglomeration of spheres.

For purposes of comparison, a comparative dentifrice designated "Composition 2" was also prepared in the same manner as Composition 1 with 20% by weight total abrasive content except the abrasive content consisted only of a precipitated silica abrasive (Zeodent 115) having the morphology shown in FIG. 2. The ingredients of Composition 2 are also listed in Table I below.

TABLE I

Dentifrice Formulations

| Ingredients | Composition 1 | Composition 2 |
| --- | --- | --- |
| Glycerin | 20.00 | 20.000 |
| Propylene glycol | 0.500 | 0.500 |
| LB9505 | 0.400 | 0.400 |
| Carrageenan CMC 2000S | 1.100 | 1.100 |
| DI water | 14.457 | 14.457 |
| Na saccharin | 0.300 | 0.300 |
| NaF | 0.243 | 0.243 |
| Sorbitol | 20.500 | 20.500 |
| Gantrez S97 liquid | 15.000 | 15.000 |
| TiO2 | 0.300 | 0.300 |
| NaOH (50%) | 1.000 | 1.000 |
| Zeodent 115 | 10.000 | 20.000 |
| Sylodent XWA 650 | 10.000 | 0 |

TABLE I-continued

Dentifrice Formulations

| Ingredients | Composition 1 | Composition 2 |
| --- | --- | --- |
| Zeodent 165 | 3.500 | 3.500 |
| SLS powder | 1.500 | 1.500 |
| Flavor | 1.200 | 1.200 |
| Total | 100.00 | 100.00 |

Compositions 1 and 2 were prepared in a jacketed, vacuum mixing tank at ambient room temperature. The glycerin and sorbitol humectants were added to the water in the mixing tank and agitation was started. The sodium fluoride salt, sodium saccharin sweetening agent, sodium carboxymethyl cellulose organic thickener, and Gantrez S-97 were added and mixing continued until a homogenous gel phase was obtained. Into the gel phase were added the $TiO_2$ pigment and the sodium hydroxide to adjust the pH. The Zeodent 165 silica thickening agent was then added to the abrasives, and the resulting mixture was added to the mixing tank under high agitation and a vacuum of about 30 mm of Hg. The triclosan was dissolved in the flavor oils to form a solution and the solution was added, with the sodium lauryl sulfate surfactant, to the mixing tank still maintaining the vacuum at about 30 mm of Hg. Mixing and vacuum continued for approximately 15 minutes. The resulting composition which was an extrudable paste, having a pH of about 7, was tubed.

The PCR of Compositions 1 and 2 was established using the modified Stookey procedure, as described hereinbefore, and the results are recorded in Table II, below. RDA values for the dentifrice compositions was determined by the Hefferren method, as described earlier, and the results also recorded in Table II.

TABLE II

| Composition No. | PCR Value | RDA Value |
| --- | --- | --- |
| 1 | 158 | 125 |
| 2 | 36 | 62 |

Referring to Table II, Composition 1 containing both the silica hydrogel abrasive of the present invention and precipitated silica abrasive exhibited a significantly higher PCR than comparative Composition 2, containing only the precipitated silica abrasive, the RDA values for Compositions 1 and 2 both being substantially below acceptable standards whereas the PCR value of Composition 1 was significantly greater than that of comparative Composition 2.

EXAMPLE II

Two silica dentifrice composition were prepared in accordance with the procedure of Example 1 and designated Compositions 3 and 4. Composition 3 contains the silica hydrogel of the present invention, while composition 4 did not, and was prepared for comparative purposes. The ingredients of Compositions 3, and 4 are listed in Table III below.

TABLE III

| Ingredients | Composition 3 | Composition 4 |
| --- | --- | --- |
| Purified water | 10.00 | 10.00 |
| Sodium monofluorophosphate | 0.760 | 0.760 |
| Sodium saccharin | 0.50 | 0.50 |
| Propylene glycol | 13.79 | 14.09 |
| Iota carrageenan | 0.250 | 0.200 |
| Sodium CMC | 0.250 | 0.200 |
| Tetrasodium pyrophosphate | 2.00 | 2.00 |
| Sodium tripolyphosphate | 3.00 | 3.00 |
| Titanium dioxide | 1.00 | 1.00 |
| Synthetic glycerin | 26.500 | 26.500 |
| Sodium hydroxide | 1.00 | 1.00 |
| Zeodent 115 (Precipitated silica) | 20.00 | 20.00 |
| Sylodent XWA 300 (Silica gel) | — | — |
| Sylodent XWA 650 (Silica gel) | 10.00 | — |
| Zeodent 165 | 1.0 | 1.80 |
| Sodium bicarbonate | 7.00 | 16.0 |
| Flavor | 0.950 | 0.950 |
| Calcium peroxide | 0.500 | 0.500 |
| Sodium lauryl sulfate | 1.5 | 1.5 |
| Total | 100.00 | 100.00 |

The PCR and RDA values of Compositions 3 and 4 are recorded in Table IV below.

TABLE IV

| Composition No. | PCR Value | RDA Value |
| --- | --- | --- |
| 3 | 188 | 136 |
| 4 | 116 | 99 |

The results recorded in Table IV, although the RDA values of both compositions were all well below the abrasivity limits set by the US Federal Drug Administration and American Dental Association, Composition 3 exhibited highly significantly greater PCR values than the comparative dentifrice Composition 4.

What is claimed is:

1. A dentifrice composition, comprising an orally acceptable vehicle containing from about 5 to about 30% by weight silica hydrogel particles, the particles containing about 10 to about 35% by weight water having:

(i) a mean particle size from about 5 to about 12 microns;
   (ii) an Einlehner hardness of from 1 to about 20;
   (iii) an oil absorption of from about 40 to less than about 100 cc/100 g;
   (iv) a BET surface area from 100 to 700 m$^2$/g of silica, the morphology of the particles being characterized by glass conchoidal fracture surfaces whereby the dentifrice composition has a RDA of 110 to 200 and a PCR from about 150 to about 300.

2. A dentifrice composition according to claim 1, wherein said composition further comprises a fluoride ion source.

3. A dentifrice composition according to claim 2, further comprising a surfactant.

4. A dentifrice composition according to claim 3, wherein said composition has a pH above about 7 and wherein the surfactant is sodium lauryl sulfate.

5. A dentifrice composition according to claim 4, further comprising from about 5% to about 70% of a humectant selected from glycerin, sorbitol, propylene glycol and mixtures thereof.

6. A dentifrice composition according to claim 1, wherein the dentifrice composition contains an antitartar or an antibacterial agent or mixture thereof, and an anionic polycarboxylate.

7. A dentifrice composition according to claim 1, wherein the dentifrice composition has an RDA from about 120 to about 170.

8. A method for reducing stain and/or plaque and inhibiting gingivitis comprising the application of a safe and effective amount of a composition according to claim 1, to the teeth and other oral surfaces.

9. A method for reducing stain and/or plaque and inhibiting gingivitis comprising the application of a safe and effective amount of a composition according to claim 1, to the teeth and other oral surfaces.

* * * * *